US Patent [19] 4,414,211
Rasmussen [45] Nov. 8, 1983

[54] HETEROCYCLIC DERIVATIVES OF GUANIDINE

[75] Inventor: Chris R. Rasmussen, Ambler, Pa.

[73] Assignee: McNeilab, Inc., Fort Washington, Pa.

[21] Appl. No.: 130,272

[22] Filed: Mar. 14, 1980

Related U.S. Application Data

[63] Continuation-in-part of Ser. No. 943,099, Sep. 18, 1978, abandoned.

[51] Int. Cl.³ ............... A61K 31/42; A61K 31/425; A61K 31/535; A61K 31/54; C07D 263/16; C07D 265/30; C07D 277/18; C07D 279/12

[52] U.S. Cl. ............... 424/246; 260/243.3; 260/244.4; 260/245.5; 260/245.7; 260/330; 260/330.6; 424/244; 424/248.51; 424/248.52; 424/248.55; 424/248.56; 424/250; 424/267; 424/270; 424/272; 424/275; 424/287; 544/53; 544/54; 544/55; 544/58.1; 544/58.5; 544/130; 544/133; 544/58.6; 544/137; 544/141; 544/58.7; 544/148; 544/159; 544/59; 544/162; 544/165; 544/60; 544/369; 546/197; 544/85; 546/205; 546/206; 544/86; 546/209; 548/193; 544/88; 548/194; 548/198; 544/96; 548/233; 544/121; 544/129

[58] Field of Search ............ 544/60, 53, 54, 55, 544/121, 129, 130, 133, 137, 141, 148, 159, 162, 165, 544/369; 424/270, 244, 246, 248.51, 248.52, 248.55, 424/248.56, 250, 267, 270, 272, 273, 282; 260/243.3, 244.4, 245.5, 245.7, 330, 330.6; 546/197, 205, 546/206, 209; 548/193, 194, 198, 233

[56] References Cited

U.S. PATENT DOCUMENTS

| | | | |
|---|---|---|---|
| 3,914,306 | 10/1975 | Douglas et al. | 424/266 X |
| 3,933,836 | 1/1976 | Yale et al. | 424/263 X |
| 4,073,636 | 2/1978 | Regel et al. | 71/92 |
| 4,211,867 | 7/1980 | Rasmussen | 544/60 |
| 4,250,173 | 2/1981 | Cantello | 424/270 |

FOREIGN PATENT DOCUMENTS

| | | |
|---|---|---|
| 2321330 | 11/1974 | Fed. Rep. of Germany . |
| 2502397 | 8/1975 | Fed. Rep. of Germany . |
| 1341245 | 12/1973 | United Kingdom . |
| 1409768 | 10/1975 | United Kingdom . |

*Primary Examiner*—Richard Raymond

[57] ABSTRACT

5-Membered, 6-membered and 7-membered heterocyclic derivatives of guanidine having hypoglycemic activity.

33 Claims, No Drawings

HETEROCYCLIC DERIVATIVES OF GUANIDINE

This application is a continuation-in-part of my co-pending application, Ser. No. 943,099, filed Sept. 18, 1978, now abandoned.

BACKGROUND OF THE INVENTION

In British Pat. No. 1,409,768, there are described several heterocyclic derivatives of guanidine in which the heterocyclic moiety is a 5- or 6-membered saturated, 1,3-diazacarbocyclic-2-ylidene. These derivatives are unsubstituted on the imino nitrogen of the guanidine moiety. In contrast, the compounds of the present invention differ by being a heterocyclic derivative of guanidine which carries a bulky substituent on the imino nitrogen of the guanidine moiety. Additional prior art, but further related, may be represented by German Offen. Nos. 2,321,330 and 2,502,397; U.S. Pat. Nos. 3,914,306; 3,933,836; and 4,073,636; and British Pat. No. 1,341,245.

DESCRIPTION OF THE PREFERRED EMBODIMENTS

This invention relates to new heterocyclic derivatives of guanidine (I) having interesting pharmacological properties and, more particularly, to such derivatives having the formula:

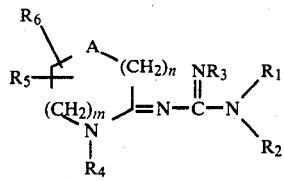

wherein:
n is the integer 0, 1, 2, 3;
m is the integer 0, 1, 2, 3, provided that n+m=1, 2, or 3;
A is a member selected from the group consisting of O and S;
$R_1$ is a member selected from the group consisting of methyl and ethyl;
$R_2$ is a member selected from the group consisting of loweralkyl (preferably methyl and ethyl), cycloalkyl having from 3 to 6 carbons (preferably cyclopentyl and cyclohexyl) and aralkyl (preferably benzyl);

taken together represents a member selected from the group consisting of:

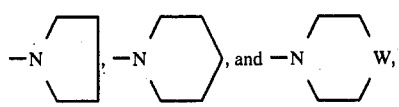

wherein

W is a member selected from the group consisting of O, S, N-loweralkyl (preferably N-methyl) and N-aryl (preferably N-phenyl); and $R_3$ is a member selected from the group consisting of:
alkyl having from 4 to 10 carbons (preferably branched), such as, for example, tert.-butyl, neopentyl, 1,1,3,3-tetramethylbutyl (tert.-octyl) and the like;
phenyl; methylenedioxyphenyl; phenyl substituted with from 1 to 3 substituents each selected from the group consisting of halo, loweralkyl and loweralkoxy; phenyl substituted with a member selected from the group consisting of hydroxy, benzyloxy, loweralkanoyloxy, nitro, trifluoromethyl, methylthio, and isopropenyl;
naphthyl;
cycloalkyl having from 5 to 8 carbons (preferably cyclopentyl and cyclohexyl); exo-2-norbornyl; endo-2-norbornyl; 1-adamantyl;
arylalkyl in which the aryl function is a member selected from the group consisting of phenyl and naphthyl and the alkyl function has from 1 to 4 carbons, such as, for example, benzyl, dl-, d-, or l-α-phenethyl, dl-, d-, or l-α-methylbenzyl, α,α-dimethylbenzyl, α,α-dimethyl-β-phenethyl, dl-, d- or l-(α-naphthyl)-ethyl and the like; and
diphenylalkyl in which the alkyl function has from 1 to 2 carbons, such as, for example, diphenylmethyl, 1,2- and 2,2-diphenylethyl and the like;
$R_4$ is a member selected from the group methyl, ethyl, n-propyl, i-propyl, n-butyl and isobutyl, preferably methyl and ethyl;
$R_5$ is H and loweralkyl, preferably H, methyl and ethyl;
$R_6$ is H and loweralkyl, preferably H, methyl and ethyl.

As used herein, the prefix "lower" indicates that the relevant group has 1 to 4 carbons and the term "halo" represents halogens of atomic weight less than 127, i.e., chloro, bromo, fluoro, and iodo.

Due to the presence of amine-like nitrogen atoms in the compounds of formula (I), acid addition salts thereof are readily obtained and such pharmaceutically-acceptable salts are included within the scope of this invention. The subject compounds (I) may be converted to their therapeutically-active nontoxic acid addition salt forms by treatment with an appropriate acid, such as, for example, an inorganic acid, such as hydrohalic acid, e.g., hydrochloric, hydrobromic and the like, or an organic acid, such as, for example, acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. Conversely, the salt form can be converted by treatment with alkali into the free base form.

The compounds of formula (I), wherein A, m, n, $R_1$, $R_2$, $R_3$, $R_4$, $R_5$, and $R_6$ (other than hydroxyphenyl and loweralkanoyloxyphenyl) are as previously defined, are prepared by reacting either a lactam salt or thiolactam salt of formula (II), wherein X is either methylthio, methoxy, or ethoxy, with a guanidine derivative of formula (III), with stoichiometric quantities of reactants being preferably employed. When X is methylthio, $Y^{\ominus}$ may be either $I^{\ominus}$, $FSO_3^{\ominus}$, or $BF_4^{\ominus}$ with $I^{\ominus}$ being preferred. When X is methoxy, $Y^{\ominus}$ may be either $BF_4^{\ominus}$ or $FSO_3^{\ominus}$. When X=ethoxy, Y is preferably $BF_4^{\ominus}$. The preparation of said guanidine derivatives (III) is described in my copending application, Ser. No. 828,561, filed Aug. 29, 1977, and entitled "Heterocyclic Derivatives of Guanidine (now U.S. Pat. No. 4,211,867)." Occasionally, it may be advantageous to add four to eight molar equivalents of potassium carbonate to the reaction mixture following addition of the guanidine (III) in order to cause the reaction to proceed toward completion. Suitable anhydrous organic solvents for conducting the reaction include loweralkanols, such as, for example, 2-propanol, tert.-butanol and the like; ethers, such as, for example, tetrahydrofuran, dioxane and the like; and lower halogenated hydrocarbons, such as, for example, chloroform, methylene chloride, 1,2-dichloroethane and the like. Ambient to reflux temperatures (about 80° C.) may generally be employed. The product (I), in the form of the corresponding HY salt, is converted to the corresponding base form (I) by conventional means, for example, by treatment with a suitable alkali such as alkali metal or alkaline earth metal hydroxides; carbonates and the like, and thence to other pharmaceutically-acceptable salt forms by techniques well-known in the art. The reaction may be illustrated as follows:

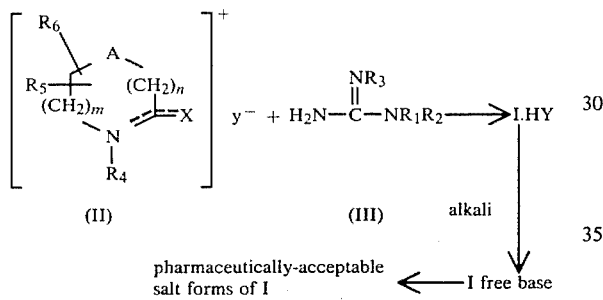

The fluoroborates of formula (II), wherein X is either SMe, OMe, or OEt and Y⊖ is BF₄⊖, may be obtained according to procedures described in the literature, e.g., See Canadian Pat. Nos. 850,116 and 950,464; U.S. Pat. No. 3,876,658; Ber. 89, 2063 (1956); and *Org. Synth.* 46, 113, 120 (1966). The fluorosulfonates of formula (II), wherein X is either SMe or OMe and Y⊖ is OSO₂F⊖ are similarly prepared. Thiolactam salts (II), wherein X is SMe and Y⊖ is I⊖, may additionally be prepared from the corresponding thiolactam (IV) (A'=S) by treatment with methyl iodide (VII). In general, an oxo- or thiooxo compound of formula IV is allowed to react with an appropriate trialkyloxonium fluoroborate (V) or methyl fluorosulfonate (VI) to give the corresponding salt (I). The reaction is preferably carried out from 0° C. to ambient temperature under an inert dry atmosphere (e.g., nitrogen, argon) in an inert anhydrous lower halohydrocarbon solvent such as, for example, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like. The reaction of thiolactams of formula IV (A'=S) with methyl iodide (VII) are legion in the literature. This type of reaction is generally carried out by treating either a suspension or solution of the thiolactam IV (A'=S) in a suitable organic solvent such as, for example, lower alkanol, methanol, ethanol, n-PrOH, t-BuOH, and the like, and ketones such as acetone, 2-butanone, and the like. The foregoing reactions may be illustrated as follows:

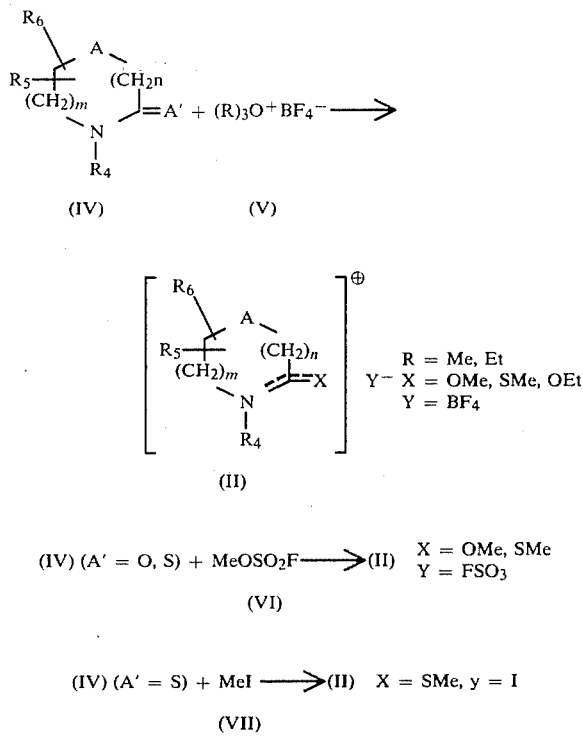

The lactams and thiolactams of formula (IV) are largely known in the literature. To the extent they are not, they may be readily prepared from the corresponding N-H lactams or thiolactams by techniques well-known in the art. In general, these techniques are represented as follows:

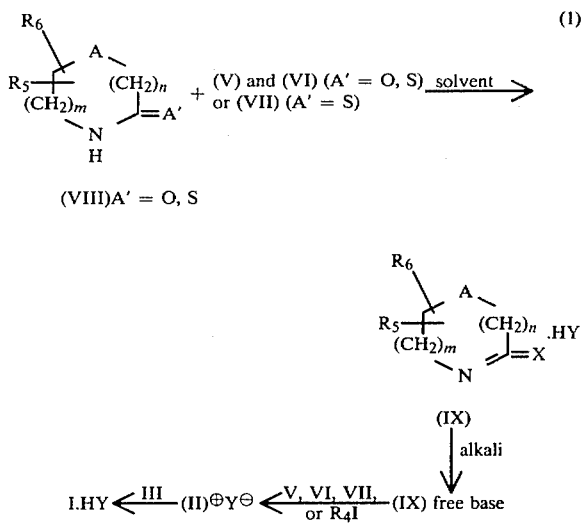

An example of this method is found in the example section of the instant application.

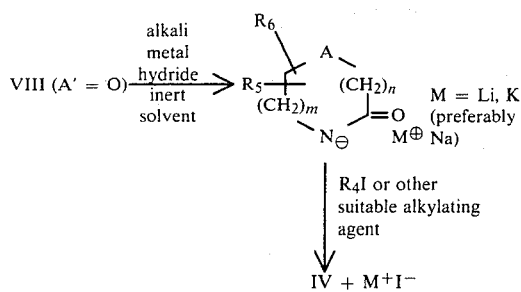

An example of this method is found in U.S. Pat. No. 3,876,658, Apr. 8, 1975, Example XL (E).

Another method of preparing those formula (I) compounds is from a lactamimide starting material of formula (X) (ZH) wherein:

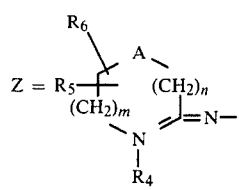

Said lactamimide, in free base form, may be reacted with an isothiocyanate of formula (XI), wherein $R_3$ is as previously described other than ortho-substituted phenyl, hydroxyphenyl and loweralkanoyloxyphenyl, in a reaction-inert organic solvent, e.g., benzene, $CH_2Cl_2$, chloroform and the like at temperatures ranging from about ambient to reflux temperatures, for about 2 to 24 hours, in approximately equimolar amounts. The thiofunction (=S) in the thus-obtained thioureas (XII), is then transferred into an alkylthio function (-SR') by reacting (XII) with an alkylating agent of the formula R'X, wherein R' is ethyl or, preferably, methyl, and X is halide, preferably, iodide, tosylate, methosulfate, mesylate, fluorosulfonate and the like. Typical solvents for such alkylations include ethers, preferably diethyl ether, tetrahydrofuran, or dioxane, lower ketones, e.g., acetone, 2-butanone and the like; halohydrocarbons and loweralkanols, preferably methylene dichloride and methanol, respectively. Methyl iodide as the alkylating agent in methanol is particularly suitable. Generally, equimolar to a large stoichiometric excess of the alkylating agent is used, the amount depending on the reactivity of the thiourea (XII) or its solubility in the solvent employed. The alkylation reaction may be carried out at temperatures ranging from ambient to reflux or in appropriate sealed vessels at higher temperatures. The alkylthio compounds of formula (XIII) in acid addition (HX) salt form are then reacted with an appropriate amine of the formula $HNR_1R_2$, wherein $R_1$, $R_2$ and $NR_1R_2$ are as previously described, preferably in a lower alkanol solvent such as isopropanol and tert.-butanol and generally at reflux temperatures of about 40°–100° C., to yield the guanidine derivatives of formula (I), in similar acid addition form, which are readily obtained as the corresponding base form by conventional treatment with suitable alkali. The foregoing reactions may be illustrated as follows:

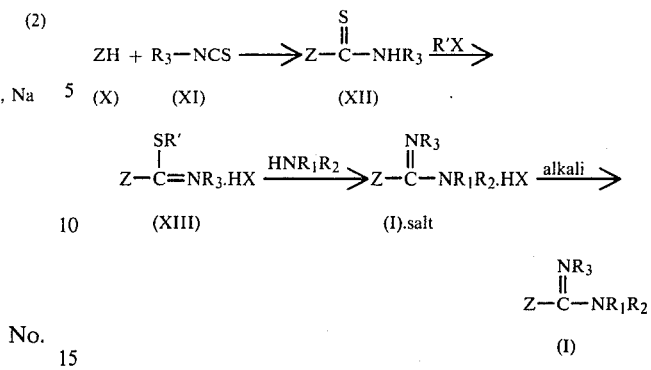

The isothiocyanates of formula XI, many of which are known, may be prepared according to the extensive processes reported in the literature for making isothiocyanates. For example, they may be obtained from the methodologies reported by M. Bogemann, et al. in *Methoden der Organische Chemie Houben-Weyl*, Eugen Müller (Ed.), Georg Thieme Verlag (Publ.) Stuttgart, Germany, Vol. 9, pp 867–884 (1955); *Preparation des Isothiocyanates Aromatiques* by A. Rasschaert, et al., *Ind. Chim.*, Belge, 32, 106 (1967); German Pat. No. 1,300,559; *J. Org. Chem.*, 36, 1549 (1971); U.S. Pat. Nos. 2,395,455 and 3,304,167; French Pat. No. 1,528,249; "A New Synthesis of Aliphatic Isothiocyanates," *Angew. Chem. Internat. Ed.*, 6, 174 (1967); *Bull. Chem. Soc. Japan*, 48, 2981 (1975); *Tetrahedron*, 29, 691 (1973); *Chem. Ber.*, 101, 1746 (1968); and *J. Indian Chem. Soc.*, 52, 148 (1975).

In the foregoing reaction of XIII with the amine, $HNR_1R_2$, it is preferred to use a stoichiometric excess of the latter, for example, in 1:1.05 to 1:2.0 molar ratios. If only a slight excess of the $HNR_1R_2$ amine is used, it may be advantageous to add a stoichiometric equivalent of a tertiary alkyl amine, e.g., $Et_3N$, in order to enhance the rate of reaction. Any by-products which may be formed during the course of the reaction can be separated from the desired formula (I) product by standard techniques known in the art, such as, for example, by fractional crystallization. In this scheme, it is preferred that $R_3$ not be phenyl substituted with one or more ortho-substituents. When one or more ortho-substituents are present, the reaction of XIII with $HNR_1R_2$ becomes sluggish. The reactions of II with a guanidine of formula III are preferred when $R_3$=ortho-substituted phenyl.

In each of the foregoing synthetic procedures for preparing formula (I) compounds, hydroxyphenyl and loweralkanoyloxyphenyl were excluded from the original definition of $R_3$. The formula (I) compounds wherein $R_3$ is hydroxyphenyl may be prepared by hydrolysis of the corresponding $R_3$=methoxyphenyl derivatives by conventional procedures, e.g., by treatment with HBr or HI and acetic acid. Acylation of the resultant $R_3$=hydroxyphenyl derivatives by an appropriate alkanoic acid in the presence of excess dicyclohexylcarbodiimide affords the corresponding $R_3$=loweralkanoyloxyphenyl derivatives of formula (I).

The subject compounds of formula (I) and the acid addition salts thereof possess valuable pharmacological properties, particularly as hypoglycemic agents. Their ability to lower blood sugar is demonstrated in the following rat glucose tolerance test, which test is a standard and extremely sensitive procedure used in the diagnosis of diabetes and hypoglycemic disease states.

In this test, male Sprague-Dawley rats (Charles River 184–250 grams) are given water ad libitum and fasted 24 hours prior to the experiment. Two to five rats are used for each test and control group. Test compounds, 1–200 mg/kg are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from all the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally). Specimens of blood are immediately deproteinized with aqueous solutions of $Ba(OH)_2$ and $ZnSO_4$ and glucose levels are determined using the glucose oxidase assay described by L. P. Cawley, at al., "Ultra Micro Chemical Analysis of Blood Glucose With Glucose Oxidase," *Amer. J. Clin. Path.*, 32, 195 (1959). The blood glucose values at each time point are expressed in terms of milligram percent (mg glucose/100 ml of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

In addition to their hypoglycemic activity, certain of the subject compounds have been found to possess antisecretory activity and/or cardiovascular activity as demonstrated in tests described in my copending patent application, Ser. No. 828,561, filed Aug. 29, 1977, and entitled "Heterocyclic Derivatives of Guanidine (now U.S. Pat. No. 4,211,867).

The subject compounds (I), in base or salt form, may be formulated into conventional liquid and solid pharmaceutical dosage forms and preparations, for example, for oral or parenteral administration, according to standard pharmaceutical techniques in the art.

The following examples are intended to illustrate, but not to limit, the scope of the present invention. Unless otherwise stated, all parts are by weight.

EXAMPLE I

N-(3-Methyl-2-thiazolidinylidene)-N'-phenylthiourea: A solution of 0.043 mole of 2-imino-3-methylthiazolidine and an equimolar amount of phenylisothiocyanate in 70 ml of dry benzene is refluxed under nitrogen for 2.5 hours. Some ether is added to the cooled reaction mixture and solids are filtered off, 9.8 g (90%). Recrystallization from acetonitrile-ether (1:1) gives 8.0 g (75%) of pure N-(3-methyl-2-thiazolidinylidene)-N'-phenylthiourea; m.p. 168.5°–170.5° C.

EXAMPLE II

By repeating the procedure of Example I, but substituting an equivalent amount of an appropriate $R_3NCS$ for the phenylisothiocyanate used therein, there are obtained the following respective N-[2-(3-methyl-thiazolidinylidene)-N'-$R_3$ thioureas of formula (XII):

| No. | $R_3$ | No. | $R_3$ |
|---|---|---|---|
| 1. | 3-F—Ph | 21. | 2,4-diMe—Ph |
| 2. | 2,4-diF—Ph | 22. | 2,4,5-triMe—Ph |
| 3. | 4-CF$_3$—Ph | 23. | 3-Et—Ph |
| 4. | 2-Cl—5-CF$_3$—Ph | 24. | 4-IsoPr—Ph |
| 5. | 4-Cl—Ph | 25. | 4-t-Bu—Ph |
| 6. | 2,4-diCl—Ph | 26. | 3-NO$_2$—Ph |
| 7. | 2,4,5-triCl—Ph | 27. | 3-SMe—Ph |
| 8. | 5-Cl—2-OMe—Ph | 28. | 1-naphthyl |
| 9. | 3-Cl—4-Me—Ph | 29. | benzhydryl |
| 10. | 4-Br—Ph | 30. | d,l-α-Me—Bz |
| 11. | 4-Br—3-Cl—Ph | 31. | α,α-dimethylphenethyl |
| 12. | 4-Br—3-Me—Ph | 32. | 2,2-diphenylethyl |
| 13. | 3-I—Ph | 33. | 1-adamantyl |
| 14. | 4-OMe—Ph | 34. | cyclopentyl |
| 15. | 2-OMe—5-Me—Ph | 35. | cyclohexyl |
| 16. | 3,5-diOMe—Ph | 36. | exo-2-norbornyl |
| 17. | 3,4-methylenedioxy-Ph | 37. | endo-2-norbornyl |
| 18. | 4-OEt—Ph | 38. | neopentyl |
| 19. | 3-OBz—Ph | 39. | tert.-octyl |
| 20. | 3-Me—Ph | 40. | 3,4,5-triOMe—Ph |

NOTE:
Me = methyl;
Et = ethyl;
IsoPr = isopropyl;
Bu = butyl;
Ph = phenyl;
Bz = benzyl.

EXAMPLE III

Methyl N-(3-methyl-2-thiazolidinylidene)-N'-phenylcarbamimidothioate hydroiodide: A suspension of 17.0 g (0.067 mole) of N-(3-methyl-2-thiazolidinylidene)-N'-phenylthiourea and 11.1 g (0.078 mole) of iodomethane in 350 ml of acetone is refluxed for one hour. The solution is cooled at room temperature overnight (about 16 hours) and solids are filtered off, 25.1 g (95.2%), m.p. 159.5°–161.5° C. Recrystallization from methanol-ether (1:1) gives pure methyl N-(3-methyl-2-thiazolidinylidene)-N'-phenylcarbamimidothioate hydroiodide; m.p. 163.5°–165° C.

EXAMPLE IV

By repeating the S-methylation procedure of Example III with each of the thioureas of Example II, the respective corresponding methyl carbamimidothioate hydroiodide salts of formula (XI) are obtained.

EXAMPLE V

N-(3-Methyl-2-thiazolidinylidene)-N'-phenyl-1-pyrrolidinecarboximidamide hydroiodide: A mixture of 0.030 mole of methyl N-(3-methyl-2-thiazolidinylidene)-N'-phenylcarbamimidothioate hydroiodide and 4.4 g (0.062 mole) of pyrrolidine in 200 ml of t-butanol is refluxed for 24 hours under a slow stream of nitrogen. Sodium hypochlorite and NaOH traps are used to remove the methyl mercaptan formed during the reaction. The reaction mixture is then cooled, ether added, and the solids formed are filtered off to give 9.3 g (75%) of product. Recrystallizations from acetone-ethyl acetate (1:1) gives 7.8 g (62%) of pure N-(3-methyl-2-thiazolidinylidene)-N'-phenyl-1-pyrrolidinecarboximidamide hydroiodide; m.p. 157.5°–160° C.

EXAMPLE VI

N-(3-Methyl-2-thiazolidinylidene)-N'-phenyl-4-morpholinecarboximidamide hydroiodide: The procedure of Example V is repeated, except that an equivalent amount of morpholine is substituted for the pyrrolidine used therein to yield the product, N-(3-methyl-2- thiazolidinylidene)-1-morpholine-N'-phenylcarboximidamide hydroiodide, m.p. (188°) 190°–191.5° C.

EXAMPLE VII

N-(4-Methoxyphenyl)-N'-(3-methyl-2-thiazolidinylidene)-1-piperidinecarboximidamide fumarate: The procedure of Example V is repeated except that an equivalent amount of piperidine is substituted for the pyrrolidine and an equivalent amount of the pseudothiouronium salt of Example IV (Compound No. 14) are utilized as reactants. Basification of the resultant HI salt with aqueous NaOH followed by treatment of the base with an equivalent amount of fumaric acid yields the product, N-(4-methoxyphenyl)-N'-(3-methyl-2-thiazolidinylidene)-1-piperidinecarboximidamide fumarate, m.p. 159.5°–160° C.

EXAMPLE VIII

By repeating the procedure of Example V, but employing an equivalent amount of an appropriate $R_1R_2NH$ amine and an equivalent amount of the appropriate pseudothiourea from Example IV as starting materials, the following respective compounds of formula (I) are obtained as the hydroiodide salt.

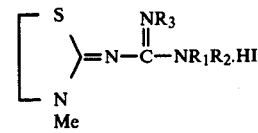

| No. | $R_3$ | $-NR_1R_2$ | No. | $R_3$ | $-NR_1R_2$ |
|---|---|---|---|---|---|
| 1 | 3-F—Ph | —N(piperidine) | 21 | 2,4-diMe—Ph | —N(N—Me piperazine) |
| 2 | 2,4-diF—Ph | —N(morpholine) | 22 | 2,4,5-triMe—Ph | —N(N—Ph piperazine) |
| 3 | 4-CF$_3$—Ph | —N(thiomorpholine) | 23 | 3-Et—Ph | —N(pyrrolidine) |
| 4 | 2-Cl—5-CF$_3$—Ph | —NEt$_2$ | 24 | 4-IsoPr—Ph | N(Me)Bz |
| 5 | 4-Cl—Ph | —NMe$_2$ | 25 | 4-t-Bu—Ph | —N(piperidine) |
| 6 | 2,4-diCl—Ph | —N(Me)Et | 26 | 3-NO$_2$—Ph | —N(morpholine) |
| 7 | 2,4,5-triCl—Ph | —N(Me)(thiazolidine-S) | 27 | 3-SMe—Ph | N(thiomorpholine) |
| 8 | 5-Cl—2-OMe—Ph | —N(Me)(thiazine-S) | 28 | 1-naphthyl | N—Et$_2$ |
| 9 | 3-Cl—4-Me—Ph | —N(N—Me piperazine) | 29 | benzhydryl | NMe$_2$ |
| 10 | 4-Br—Ph | —N(N—Ph piperazine) | 30 | d,l-α-Me—Bz | N(Me)Et |
| 11 | 4-Br—3-Cl—Ph | —N(pyrrolidine) | 31 | α,α-diMe—phenethyl | N(Me)(thiazolidine-S) |

-continued

| No. | R₃ | —NR₁R₂ | No. | R₃ | —NR₁R₂ |
|---|---|---|---|---|---|
| 12 | 4-Br—3-Me—Ph | —N(Me)CH₂Ph | 32 | 2,2-diphenyl-ethyl | N(Me)—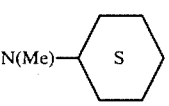 |
| 13 | 3-I—Ph | 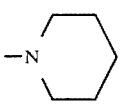 | 33 | 1-adamantyl |  |
| 14 | 4-OMe—Ph | 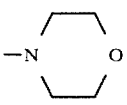 | 34 | cyclopentyl | 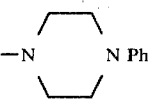 |
| 15 | 2-OMe—5-Me—Ph | 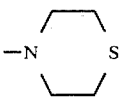 | 25 | cyclohexyl | 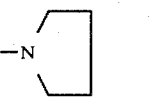 |
| 16 | 3,5-diOMe—Ph | —NEt₂ | 36 | exo-2-norbornyl | 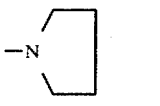 |
| 17 | 3,4-methylene-dioxy-Ph | —NMe₂ | 37 | endo-2-norbornyl | 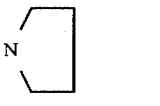 |
| 18 | 4-OEt—Ph | N(Me)Et | 38 | neopentyl | 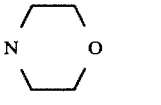 |
| 19 | 3-OBz—Ph | N(Me)—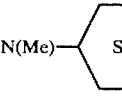 | 39 | tert-octyl | 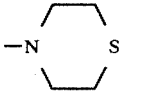 |
| 20 | 3-Me—Ph | N(Me)—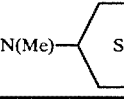 | 40 | 3,4,5-triOMe—Ph | N(Me)CH₂Ph |

EXAMPLE IX

N-(3-Methyl-2-oxazolidinylidene)-N'-phenyl-1-pyrrolidinecarboximidamide fumarate: Triethyloxonium fluoroborate is prepared from 1.85 g of epichlorohydrin in 7 ml of ether and 3.74 g (0.027 mole) of boron trifluoride etherate in 3 ml of ether. The solid triethyloxonium fluoroborate is dissolved in 10 ml of dry methylene chloride and treated under nitrogen with 2.02 g (0.020 mole) of 3-methyloxazolidin-2-one in 20 ml of methylene chloride. The reaction mixture is stirred under nitrogen at room temperature overnight. A 50 ml methylene chloride solution of 0.020 mole of N-phenyl-1-pyrrolidinecarboximidamide free base (obtained from the corresponding hydrochloride salt with 50% sodium hydroxide and dried over potassium carbonate) is added to the reaction mixture and stirred at room temperature overnight.

The solvent is removed in vacuo and the resulting HBF₄ salt is recrystallized from 2-propanol/ether (1:1) to give 4.65 g of N-(3-methyl-2-oxazolidinylidene)-N'-phenyl-1-pyrrolidinecarboximidamide HBF₄ as a white solid, m.p. 142°–144° C. Conversion to the free base is done by partitioning the salt between 3 N sodium hydroxide and methylene chloride. The combined organic layers are dried over potassium carbonate and the solvent removed in vacuo. The resulting oil 2.9 g is dissolved in 2-propanol and treated with an equimolar amount of fumaric acid in the same solvent. Recrystallization from 2-propanol/ether gives 4.08 g of pure N-(3-Methyl-2-oxazolidinylidene)-N'-phenyl-1-pyrrolidinecarboximidamide fumarate, m.p. 160°–162° C.

EXAMPLE X

N-(2,3,5,6-Tetrahydro-4-methyl-1,4-oxazine-3-ylidene)-N'-phenyl-1-pyrrolidinecarboximidamide fumarate: Triethyloxonium fluoroborate is prepared from 3.70 g (0.040 mole) of epichlorohydrin in 14 ml of ether and 7.58 g (0.054 mole) of boron trifluoride etherate in 6 ml of ether. The solid triethyloxonium fluoroborate is dissolved in 20 ml of dry methylene chloride and treated under nitrogen with 4.60 g (0.040 mole) of 2,3,5,6-tetrahydro-4-methyl-1,4-oxazine-2-one in 20 ml of dry methylene chloride. The reaction mixture is stirred under nitrogen at room temperature overnight. A 50 ml methylene chloride solution of N-phenyl-1-pyrrolidinecarboximidamide free base (obtained from 12.7 g, 0.040 mole of the corresponding hydroiodide with 50% sodium hydroxide and dried over potassium carbonate) is added to the reaction mixture and stirred at room temperature overnight.

The solvent is removed in vacuo and the resulting HBF$_4$ salt is recrystallized from 2-propanol/ether (1:1) to give 10.3 g of white solid. Conversion to the free base is done by partitioning the salt between 3 N sodium hydroxide and methylene chloride. The combined organic layers are dried over potassium carbonate and the solvent removed in vacuo. The resulting oil, 9.0 g (0.0315 mole, 78%) is dissolved in 2-propanol and treated with an equimolar amount of fumaric acid in the same solvent. The salt is recrystallized from ethanol-ether to give 8.5 g of pure N-(2,3,5,6-Tetrahydro-4-methyl-1,4-oxazine-3-ylidene)-N'-phenyl-1-pyrrolidinecarboximidamide fumarate, m.p. 191°–193° C.

EXAMPLE XI

By following the procedure of Example IX for products having the ring function, 3-methyl-2-oxazolidinylidene, and the procedure of Example X for products having the ring function, 2,3,5,6-tetrahydro-4-methyl-1,4-oxazine-3-ylidene, except that an equivalent amount of an appropriate guanidine of formula (III) is substituted for the N-phenyl-1-pyrrolidinecarboximidamide of each Example, the following respective products of formula (I) are obtained, converted to the indicated acid addition (HX) salt.

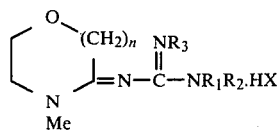

| No. | R$_3$ | —NR$_1$R$_2$ | HX |
|---|---|---|---|
| n = zero: | | | |
| 1 | Ph | —N(CH$_2$CH$_2$)$_2$S (thiomorpholino) | HI |
| 2 | 3,4-methylenedioxy-Ph | piperidino | HBr |
| 3 | 4-n-Bu—Ph | —NEt$_2$ | fumarate |
| 4 | 4-OBz—Ph | pyrrolidino | HI |
| 5 | 4-Me—Ph | pyrrolidino | HCl |
| 6 | 3-Cl—Ph | morpholino | H$_3$PO$_4$ |
| 7 | 4-NO$_2$—Ph | pyrrolidino | H$_2$SO$_4$ |
| 8 | benzhydryl | morpholino | maleate |
| 9 | exo-2-norbornyl | pyrrolidino | HI |
| 10 | 3,4-diOMe—Ph | —NMe$_2$ | TsOH |
| 11 | α,α-diMe—Bz | —NEt$_2$ | fumarate |
| 12 | 3,4-diCl—Ph | pyrrolidino | H$_3$PO$_4$ |
| 13 | 1-naphthyl | —N(Me)(thiazolinyl) | HI |
| 14 | 4-OMe—Ph | pyrrolidino | HI |
| 15 | Bz | piperidino | HI |
| 16 | cyclopentyl | —N(Me)Bz | fumarate |
| 17 | 3,4,5-triOMe—Ph | pyrrolidino | HI |
| n = 1 | | | |
| 18 | Ph | —N(Me)(thiazinyl) | HI |
| 19 | endo-2-norbornyl | —NEt$_2$ | HBr |
| 20 | 3-CF$_3$—Ph | —N(Me)(thiazinyl) | HNO$_3$ |

-continued

| No. | R₃ | —NR₁R₂ | HX |
|---|---|---|---|
| 21 | 4-OMe—Ph | pyrrolidine | HI |
| 22 | 4-SMe—Ph | thiomorpholine | fumarate |
| 23 | 4-NO₂—Ph | pyrrolidine | maleate |
| 24 | 4-OBz—Ph | pyrrolidine | HI |
| 25 | d,l-α-Me—Bz | morpholine | HI |
| 26 | cyclohexyl | —NEt₂ | succinate |
| 27 | tert-octyl | morpholine | HCl |
| 28 | 1,2-diphenylethyl | pyrrolidine | HNO₃ |
| 29 | -4-OMe—2,5-diMe—Ph | —NMe₂ | HCl |
| 30 | α,α-diMe—phenethyl | thiomorpholine | HNO₃ |
| 31 | 1-adamantyl | pyrrolidine | HI |
| 32 | 3,4-diCl—Ph | —NEt₂ | HCl |
| 33 | 1-naphthyl | —N(Me)Bz | fumarate |
| 34 | neopentyl | pyrrolidine | HI |
| 35 | 2,4,5-triCl—Ph | —NEt₂ | fumarate |

EXAMPLE XII

N-(3-Methyl-2-oxazolidinylidene)-N'-phenyl-1-pyrrolidine-carboximidamide fumarate: To a solution of 3-methyloxazolidin-2-one, 2.02 g (0.02 mole), in dry methylene chloride under dry nitrogen is added 2.28 g (0.02 mole) of methyl fluorosulfonate in one portion. After stirring 3 hrs, 0.02 mole of N-phenyl-1-pyrrolidinecarboximidamide free base in dry methylene chloride is added. After stirring at room temperature overnight, the solution is shaken with excess cold 3 N NaOH. The organic layer is separated and dried over K₂CO₃, filtered, and the solvent removed in vacuo to afford the crude base. Addition of an equimolar amount of fumaric acid to a solution of the free base in isopropanol, followed by recrystallization from isopropanol/ether affords pure N-(3-methyl-2-oxazolidinylidene)-N'-phenyl-1-pyrrolidinecarboximidamide fumarate; m.p. 160°–162° C.

EXAMPLE XIII

N-{[(2,3,5,6-Tetrahydro)-4-methyl]-1,4-thiazin-3-ylidene}-N'-(4-methoxyphenyl)-1-piperidinecarboximidamide hydroiodide: Triethyloxonium fluoroborate (0.07 mole) is prepared from 13.2 g (0.093 mole) of borontrifluoride etherate and 6.48 g (0.07 mole) of epichlorohydrin in anhydrous ether under dry nitrogen. The resultant oily crystals are washed with fresh dry ether by decantation and dissolved in dry methylene chloride. To this solution is added 4.25 g (0.0324 mole) of 4-methylthiamorpholin-3-one (2,3,5,6-tetrahydro-4-methyl-1,4-thiazin-3-one) and the mixture is stirred 2 hr at room temperature. Then 0.027 mole of N-(4-methoxyphenyl)-1-piperidinecarboximidamide in 50 ml of dry CH₂Cl₂ and 11.2 g (0.08 mole) of anhydrous potassium carbonate are added. The resulting mixture is stirred overnight at ambient temperatures.

The reaction mixture is filtered and the filtrate is shaken with cold 20% aqueous NaOH. The organic layer is separated and dried over K₂CO₃, filtered and the solvent removed in vacuo to give an oily residue. Kugelrohr distillation (air bath temperature 120°–200° C.) removes any unchanged N-(4-methoxyphenyl)-1-piperidinecarboximidamide. The residue of desired product in base form is converted to the HI salt and recrystallized to give pure N-{[(2,3,5,6-tetrahydro)-4-methyl]-1,4-thiazin-3-ylidene}-N'-(4-methoxyphenyl)-1-piperidinecarboximidamide hydroiodide.

EXAMPLE XIV

The procedure of Example XIII is followed except that an equivalent quantity of an appropriate guanidine of formula (III) is substituted for the N-(4-methoxyphenyl)-1-piperidinecarboximidamide used therein to yield the following respective products of formula (I), converted to the indicated acid addition (HX) salt.

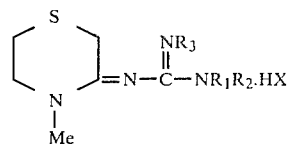

| No. | R₃ | —NR₁R₂ | HX |
|---|---|---|---|
| 1 | Ph | —NEt₂ | HI |
| 2 | benzhydryl | pyrrolidine | base |

-continued

| No. | R₃ | —NR₁R₂ | HX |
|---|---|---|---|
| 3 | 3-Cl—Ph | 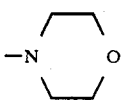 —N□O | fumarate |
| 4 | 2,4,5-triCl—Ph | 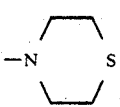 —N□S | HCl |
| 5 | Bz | —NMe₂ | HCl |
| 6 | 1-naphthyl | 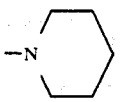 —N⬡ | HBr |
| 7 | dl-α-Me—Bz | 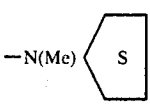 —N(Me)⬠S | base |
| 8 | 4-NO₂—Ph | —N(Me)Bz | HI |
| 9 | 3,4-diOMe—Ph | 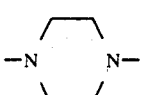 —N□N—Ph | HCl |
| 10 | cyclohexyl | 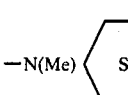 —N(Me)⬠S | HCl |

EXAMPLE XV

N-{[(2,3,5,6-Tetrahydro)-4-methyl]-1,4-thiazin-3-ylidene}-N'-(4-hydroxyphenyl)-1-piperidinecarboximidamide hydroiodide: A solution of 0.01 mole of the R₃=4-methoxyphenyl derivative of Example XIII in 7 g of 50% HI and 7 g of glacial acetic acid is heated under reflux for 6 hr. The solvent and excess HI are removed in vacuo to yield the product, N-{[(2,3,5,6-tetrahydro)-4-methyl]-1,4-thiazin-3-ylidene}-N'-(4-hydroxyphenyl)-1-piperdinecarboximidamide hydroiodide.

EXAMPLE XVI

By following the hydrolysis procedure of Example XV, except that an equivalent amount of an appropriate R₃=4-methoxyphenyl derivative is utilized as the precursor to be hydrolyzed, the following respective R₃=hydroxphenyl derivatives of formula (I) are obtained (converted to free base):

1. Precursor: Compound No. 14 of Example VIII.
    Product: N—(4-Hydroxyphenyl)-N'—(3-methyl-2-thiazolidinylidene)-4-morpholinecarboximidamide.
2. Precursor: Compound No. 14 of Example XI.
    Product: N—(4-Hydroxyphenyl)-N'—(3-methyl-2-oxazolidinylidene)-1-pyrrolidinecarboximidamide.
3. Precursor: Compound No. 21 of Example XI.
    Product: N—(4-Hydroxyphenyl)-N'—(2,3,5,6-tetrahydro-4-methyl-1,4-oxazine-3-ylidene)-1-pyrrolidinecarboximidamide.

EXAMPLE XVII

N-(4-Hydroxyphenyl)-N'-(3-methyl-2-thiazolidinylidene)-1-piperidinecarboximidamide hydroiodide: To 2.56 g (7.7 mmoles) of the R₃=4-methoxyphenyl derivative of Example VII (as the free base) is added 4.92 g (19.2 mmoles) of 50% HI and 4.0 g of glacial acetic acid. The resulting mixture is heated (oil bath) under reflux overnight. The excess HI and acetic acid are removed in vacuo and the residue is washed several times with ether and then scratched to afford crystals which are suspended in t-BuOH, filtered, and washed with ether to furnish the crude product; m.p. 174°–176° C. Recrystallization from t-BuOH (containing a little MeOH to help dissolve the crystals and then boiling off the MeOH) gives pure N-(4-hydroxyphenyl)-N'-(3-methyl-2-thiazolidinylidene)-1-piperidinecarboximidamide hydroiodide which is dried in vacuo; m.p. 175°–177° C.

EXAMPLE XVIII

N-(4-Acetyloxyphenyl)-N'-(3-methyl-2-oxazolidinylidene)-1-pyrrolidinecarboximidamide hydroiodide: A solution of 4.16 g (0.01 mole) of N-(4-hydroxyphenyl)-N'-(3-methyl-2-oxazolidinylidene)-1-pyrrolidinecarboximideamide hydroiodide in 10 ml of glacial acetic acid and 20 ml of acetone is treated with 20.6 g (0.1 mole) of dicyclohexylcarbodiimide at 20° C. under argon. After stirring at ambient temperatures overnight, the formed dicyclohexylurea is removed by filtration and the filtrate is taken to dryness in vacuo. Trituration with ether removes excess carbodiimide affording as the residue N-(4-acetyloxyphenyl)-N'-(3-methyl-2-oxazolidinylidene)-1-pyrrolidinecarboximidamide hydroiodide.

EXAMPLE XIX

The O-acylation procedure of Example XVIII is followed, except that an equivalent amount of an appropriate R₃=4-hydroxyphenyl derivative of Examples XV and XVI is used as the starting material to be acylated, to yield as respective products the following R₃=acetyloxyphenyl derivatives of formula (I):
1. N-(acetyloxyphenyl)-N'-[(2,3,5,6-tetrahydro)-4-methyl]-1,4-thiazine-3-ylidine-1-piperidinecarboximidamide HI.
2. N-(acetyloxyphenyl)-N'-(3-methyl-2-thiazolidinylidene)-4-morpholinecarboximidamide HI.
3. N-(acetyloxyphenyl)-N'-(2,3,5,6-tetrahydro-4-methyl-1,4-oxazine-3-ylidene)-1-pyrrolidinecarboximidamide HI.

EXAMPLE XX 4,5-Dihydro-2-(methylthio)-3-methylthiazolium iodide: 4,5-Dihydro-2-(methylthio)thiazole monohydroiodide (570 g, 2.18 moles) was treated with 3 N sodium hydroxide, extracted with methylene chloride, dried over potassium carbonate, and the solvent removed in vacuo to afford 324 g of the free base as a light clear oil. The oil was dissolved in 1.5 l of acetone, filtered, and treated with 707 g (5.0 moles) of iodomethane. The mixture was stirred at room temperature for ½ hour, then heated under reflux for ½ hour, and finally stirred overnight at room temperature. 473 g. (79%) of an off-white solid was filtered and recrystallized from a mixture of methanol-ethanol (~1:1)-ether to afford 443 g (74%) of 4,5-dihydro-2-(methylthio)-3-methyl-thiazolium iodide as a white solid, m.p. (125) 137°-140° C. (dec.); m.p. (125) 132° C. [Batty, et al., *J. Chem. Soc.*, 786 (1949)].

EXAMPLE XXI

A. N-(3-Methyl-2-thiazolidinylidene)-N'-phenyl-4-morpholinecarboximidamide hydroiodide: A solution of 21.66 g (0.065 mol) of N'-phenyl-4-morpholinecarboximidamide hydroiodide in methylene chloride (separatory funnel) was shaken with excess aqueous NaOH (20%). The organic layer was separated, dried over anhydrous $K_2CO_3$, filtered, and the solvent removed in vacuo affording the free base. To the free base was added 150 ml of tert.-BuOH followed by 0.065 mol of 3-methyl-2-methylthio-2-thiazolinium iodide [J. W. Batty and B. C. L. Weedon, *J. Chem. Soc.*, 786 (1949)]. The resulting mixture was heated under reflux for 1 hour, during which time, crystals of the title compound began to separate. The generated methyl mercaptan was trapped by a series of 2 NaOH (30%) and 1 NaOCl (5%) traps. After cooling, the crystals were collected, washed with fresh t-BuOH and ether, then dried, affording 23.4 g (83%) of crude product. One recrystallization from t-BuOH-ether gave 21.2 g (75%) of pure product which was essentially identical to the product of Example VI by m.p., IR, UV, and NMR.

B. Conversion of N-(3-methyl-2-thiazolidinylidene)-N'-phenyl-4-morpholinecarboximidamide hydroiodide, 20.3 g, to the free base in methylene chloride by treatment with excess 20% NaOH, followed by drying ($K_2CO_3$), filtration, and solvent removal in vacuo, gave the free base as a white crystalline solid which was used without further purification to obtain the following salts.

HCl, prepared in i-PrOH by addition of ethereal HCl, and recrystallized from t-BuOH (minimal amount) ether; m.p. 219.5°-221° C. Anal. Calcd. for $C_{15}H_{20}N_4OS.HCl$ (304.41/340.87); C, 52.85; H, 6.21; N, 16.44. Found: C, 52.85; H, 6.23; N, 16.42.

$H_2SO_4$, prepared in i-PrOH by addition of 1 molar equivalent of $H_2SO_4$ and recrystallized from i-PrOH-ether; m.p. 151.5°-153° C. Anal. Calcd. for $C_{15}H_{20}N_4OS.H_2SO_4$ (304.41/402.48): C, 44.76; H, 5.51; N, 13.92. Found: 44.76; H, 5.52; N, 13.91.

E-2-Butenedioate (fumarate), prepared in MeOH by addition of 1 mole equivalent of E-2-butenedioic acid, and recrystallization from i-PrOH; m.p. 166°-168.5° C. Anal. Calcd. for $C_{15}H_{20}N_4\text{-}OS.C_4H_4O_4$ (304.41/420.48); C, 54.27; H, 5.75; N, 13.32. Found: C, 54.18; H, 5.83; N, 13.28.

Methanesulfonate (mesylate), prepared in t-BuOH by addition of 1 mole equivalent of methanesulfonic acid, and recrystallized from t-BuOH-ether; m.p. 132.5°-133.5° C. Anal. Calcd. for $C_{15}H_{20}N_4OS.C\text{-}H_4O_3S$ (304.41/400.51): C, 47.98; H, 6.04; N, 13.99. Found: C, 48.00; H, 6.08; N, 13.99.

EXAMPLE XXII

N'-(4-Methylphenyl)-N-(3-methyl-2-thiazolidinylidene)-4-morpholinecarboximidamide monohydroiodide: A solution of 2.19 g (0.01 mole) of N'-(4-methylphenyl)-4-morpholinecarboximidamide and 2.85 g (0.0104 moles) of 3-methyl-2-methylthio-2-thiazolinium iodide (prepared by the method of J. W. Batty and B. C. L. Weedon, *J. Chem. Soc.*, 786 (1949) was heated under reflux in 25 ml of tert-butanol for 1.5 hours. Upon cooling, a white crystalline solid separated, and was recrystallized twice from ethanol-ether to afford 3.00 g (67%) of N'-(4-methylphenyl)-N-(3-methyl-2-thiazolidinylidene-4-morpholinecarboximidamide monohydroiodide as a white solid homogeneous on TLC, m.p. (175) 186°-188° C. Anal. Calcd. for $C_{16}H_{22}N_4OS.HI$ (318.44/462.76): C, 43.06; H, 5.19; N, 12.55. Found: C, 43.05; H, 5.21; N, 12.56.

| $\lambda_{Max}^{MeOH}$ | 257.5 nm | ($\epsilon$ = 14,200) |
|---|---|---|
| | 267 nm (shoulder) | ($\epsilon$ = 12,500). |

TLC conditions were silica GF 250$\mu$ plates eluting with MeOH/aq $NH_3$ (98/2).

EXAMPLE XXIII

N-(3-Methyl-2-thiazolidinylidene)-N'-(3,4-methylenedioxyphenyl)-4-morpholinecarboximidamide monohydroiodide: A suspension of 19.46 g (0.0445 moles) of methyl-N'-(3,4-methylenedioxyphenyl)-N-(3-methyl-2-thiazolidinylidene)carbamidimidothioate monohydroiodide and 11.63 g (0.1335 mole) of morpholine in 200 ml of tert-butanol was heated under reflux for 72 hours. The reaction mixture was cooled, ether added, and 20.1 g (95%) of a white solid was filtered. Recrystallization from methanol-ethanol-ether afforded 18 g (85%) of N-(3-methyl-2-thiazolidinylidene)-N'-(3,4-methylenedioxyphenyl)-4-morpholinecarboximidamide monohydroiodide as a white crystalline solid homogeneous on TLC, m.p. 215°-218° C. Anal. Calcd. for $C_{16}H_{20}N_4O_3S.HI$: C, 40.35; H, 4.44; N, 11.76. Found: C, 40.35; H, 4.24; N, 11.80.

| $\lambda_{Max}^{MeOH}$ | 217.5 nm | ($\epsilon$ = 33,100) |
|---|---|---|
| | 251 nm | ($\epsilon$ = 16,500) |
| | 285 nm inflection | ($\epsilon$ = 8,200). |

TLC conditions were silica GF 250$\mu$ plates eluting with MeOH/aq $NH_3$ (98/2).

EXAMPLE XXIV

A. Reaction of various anilines with benzoylisothiocyanate in refluxing acetone according to Belgian Pat. No. 852,565, Sept. 19, 1977, afford the following benzoylthioureas.

1. N-Benzoyl-N'-2-chlorophenylthiourea, m.p. 145°-146.5° C.;
2. N-Benzoyl-N'-2-methylphenylthiourea, m.p. 118°-120° C.;
3. N-Benzoyl-N'-2-ethylphenylthiourea, m.p. 95°-97° C.;
4. N-Benzoyl-N'-2-isopropylphenylthiourea, m.p. 143°-145° C.;
5. N-Benzoyl-N'-2-isopropenylphenylthiourea, m.p. 123°-124° C.;
6. N-Benzoyl-N'-2-chloro-4-methylphenylthiourea, m.p. 142°-145° C.;
7. N-Benzoyl-N'-5-chloro-2-methylphenylthiourea;
8. N-Benzoyl-N'-2-bromophenylthiourea, m.p. 137°-138.5° C.;
9. N-Benzoyl-N'-5-chloro-2-methoxyphenylthiourea, m.p. 160°-160.5° C.;
10. N-Benzoyl-N'-4-methoxy-2-methylphenylthiourea;

B. Hydrolysis of the above benzoylthioureas in 20% NaOH at 80°–90° C. according to Belgian Pat. No. 852,565, Sept. 19, 1977, gives the following thioureas:
1. 2-Chlorophenylthiourea, m.p. 143°–145° C.;
2. 2-Methylphenylthiourea, m.p. 159.5°–161.5° C.;
3. 2-Isopropylphenylthiourea, m.p. 133°–135° C.;
4. 2-Isopropenylphenylthiourea, m.p. 174°–176° C.;
5. 2-Chloro-4-methylphenylthiourea, m.p. 162°–165° C.;
6. 5-Chloro-2-methylphenylthiourea;
7. 2-Ethylphenylthiourea, m.p. 162°–165° C.;
8. 2-Bromophenylthiourea, m.p. 130°–132.5° C.;
9. 5-Chloro-2-methoxyphenylthiourea, m.p. (143) 144.5°–145.5° C.;
10. 4-Methoxy-2-methylphenylthiourea.

C. Treatment of each of the above thioureas with an S-methylating agent, preferably methyl iodide, according to Belgian Pat. No. 852,565, Sept. 19, 1977, affords the respective methyl carbamimidothioates as their HI salts.
1. Methyl N-2-chlorophenylcarbamimidothioate hydroiodide, m.p. 161.5°–165° C.;
2. Methyl N-2-methylphenylcarbamimidothioate hydroiodide, m.p. 127°–128° C.;
3. Methyl N-2-isopropylphenylcarbamimidothioate hydroiodide, m.p. 106°–109° C.;
4. Methyl N-2-isopropenylphenylcarbamimidothioate hydroiodide, m.p. 152°–154° C.;
5. Methyl N-2-chloro-4-methylphenylcarbamimidothioate hydroiodide, m.p. 150°–152° C.;
6. Methyl N-5-chloro-2-methylphenylcarbamimidothioate hydroiodide, m.p. 173°–176° C.;
7. Methyl N-2-ethylphenylcarbamimidothioate hydroiodide, m.p. 125°–128° C.;
8. Methyl N-2-bromophenylcarbamimidothioate hydroiodide, m.p. 154°–156° C.;
9. Methyl N-5-chloro-2-methoxyphenylcarbamimidothioate hydroiodide, m.p. (152) 156.5°–158.5° C.;
10. Methyl N-4-methoxy-2-methylphenylcarbamimidothioate hydroiodide.

D. Reaction of each of the above methylcarbamimidothioate esters as their HI salts with an appropriate $HNR_1R_2$ amine according to the directions in Belgian Pat. No. 852,565, Sept. 19, 1977, affords the following respective carboximidamides.
1. N-2-chlorophenyl-1-pyrrolidinecarboximidamide hydroiodide, m.p. 133°–134° C.;
2. N-2-chlorophenyl-4-morpholinecarboximidamide (free base), m.p. 88°–91° C.;
3. N-2-methylphenyl-1-pyrrolidinecarboximidamide hydroiodide, m.p. 150.5°–152° C.;
4. N-2-methylphenyl-4-morpholinecarboximidamide hydroiodide;
5. N-2-isopropylphenyl-1-pyrrolidinecarboximidamide hydroiodide, m.p. 164.5°–166.5° C.;
6. N-2-isopropylphenyl-4-morpholinecarboximidamide hydroiodide, m.p. 158°–160° C.;
7. N-2-isopropenylphenyl-1-pyrrolidinecarboximidamide hydroiodide, m.p. 171.5°–173° C.;
8. N-2-isopropenylphenyl-4-morpholinecarboximidamide hydroiodide, m.p. 179°–181° C.;
9. N-2-chloro-4-methylphenyl-1-pyrrolidinecarboximidamide hydroiodide, m.p. 162°–166° C.;
10. N-2-chloro-4-methylphenyl-4-morpholinecarboximidamide hydroiodide, m.p. 214°–217° C.;
11. N-2-chloro-4-methylphenyl-4-thiamorpholinecarboximidamide hydroiodide;
12. N-5-chloro-2-methylphenyl-1-pyrrolidinecarboximidamide hydroiodide, m.p. 271°–273° C.;
13. N-4-chloro-2-methylphenyl-4-morpholinecarboximidamide hydroiodide, m.p. 250°–252° C.;
14. N-2-ethylphenyl-1-pyrrolidinecarboximidamide hydrochloride, m.p. 196°–197° C.;
15. N-2-ethylphenyl-4-morpholinecarboximidamide hydroiodide, m.p. 210°–212° C.;
16. N-2-bromophenyl-1-pyrrolidinecarboximidamide hydroiodide, m.p. 172.5°–174.5° C.;
17. N-2-bromophenyl-4-morpholinecarboximidamide hydroiodide, m.p. 185°–192° C.;
18. N-5-chloro-2-methoxyphenyl-1-pyrrolidinecarboximidamide hydroiodide, m.p. (185) 191°–192.5° C.;
19. N-5-chloro-2-methoxyphenyl-4-morpholinecarboximidamide hydroiodide;
20. N-4-methoxy-2-methylphenyl-1-pyrrolidinecarboximidamide hydroiodide;
21. N-4-methoxy-2-methylphenyl-4-thiamorpholinecarboximidamide hydroiodide.

EXAMPLE XXV

According to the teachings of Example XXII, reaction of 3-methyl-2-methylthio-2-thiazolinium iodide with each of the carboximidamides of the preceding example in their respective free base forms affords the following products each as their hydroiodide salts.
1. N-2-Chlorophenyl-N'-3-methyl-2-thiazolidinylidene-1-pyrrolidinecarboximidamide;
2. N-2-Chlorophenyl-N'-3-methyl-2-thiazolidinylidene-4-morpholinecarboximidamide;
3. N-2-methylphenyl-N'-3-methyl-2-thiazolidinylidene-1-pyrrolidinecarboximidamide;
4. N-2-methylphenyl-N'-3-methyl-2-thiazolidinylidene-4-morpholinecarboximidamide;
5. N-2-Isopropylphenyl-N'-3-methyl-2-thiazolidinylidene-1-pyrrolidinecarboximidamide;
6. N-2-Isopropylphenyl-N'-3-methyl-2-thiazolidinylidene-4-morpholinecarboximidamide;
7. N-2-Isopropylphenyl-N'-3-methyl-2-thiazolidinylidene-1-pyrrolidinecarboximidamide;
8. N-2-Isopropenylphenyl-N'-3-methyl-2-thiazolidinylidene-4-morpholinecarboximidamide;
9. N-2-Chloro-4-methylphenyl-N'-3-methyl-2-thiazolidinylidene-1-pyrrolidinecarboximidamide;
10. N-2-Chloro-4-methylphenyl-N'-3-methyl-2-thiazolidinylidene-4-morpholinecarboximidamide;
11. N-2-Chloro-4-methyl-N'-3-methyl-2-thiazolidinylidene-4-thiamorpholinecarboximidamide;
12. N-5-Chloro-2-methyl-N'-3-methyl-2-thiazolidinylidene-1-pyrrolidinecarboximidamide;
13. N-5-Chloro-2-methyl-N'-3-methyl-2-thiazolidinylidene-4-morpholinecarboximidamide;
14. N-2-Ethylphenyl-N'-3-methyl-2-thiazolidinylidene-1-pyrrolidinecarboximidamide;
15. N-2-Ethylphenyl-N'-3-methyl-2-thiazolidinylidene-4-morpholinecarboximidamide;
16. N-2-Bromophenyl-N'-3-methyl-2-thiazolidinylidene-1-pyrrolidinecarboximidamide;
17. N-2-Bromophenyl-N'-3-methyl-2-thiazolidinylidene-4-morpholinecarboximidamide;
18. N-5-Chloro-2-methoxyphenyl-N'-3-methyl-2-thiazolidinylidene-1-pyrrolidinecarboximidamide;
19. N-5-Chloro-2-methoxyphenyl-N'-3-methyl-2-thiazolidinylidene-4-morpholinecarboximidamide;

20. N-4-Methoxy-2-methylphenyl-N'-3-methyl-2-thiazolidinylidene-1-pyrrolidinecarboximidamide;
21. N-4-Methoxy-2-methylphenyl-N'-3-methyl-2-thiazolidinylidene-4-thiamorpholinecarboximidamide.

The above products may each be converted to their respective free base forms and thence to other pharmaceutically-acceptable salt forms.

EXAMPLE XXVI

A. Treatment of the appropriate thiolactam with methyl iodide, according to the teaching of Example XX, affords the following S-methyl thiolactim ethers as their respective free base forms.

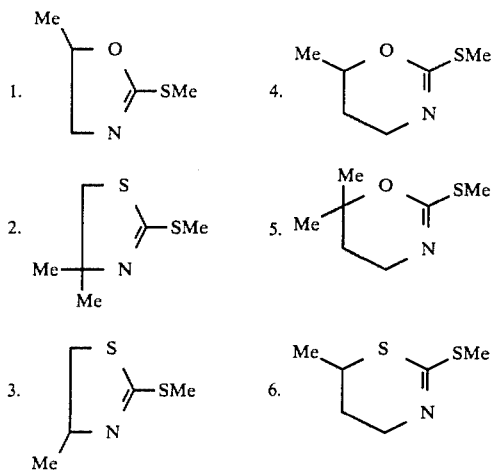

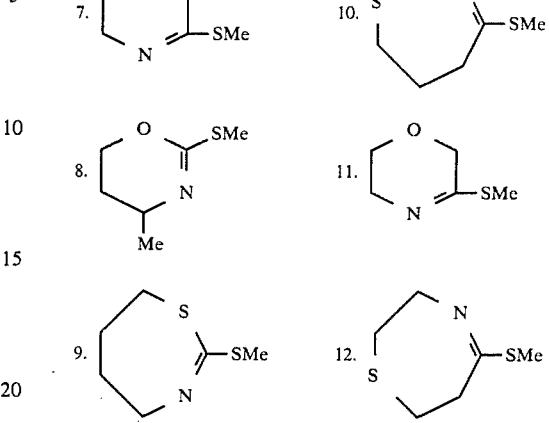

B. According to the teachings of *Org. Synth. Coll.,* Vol. X, p 780 (1973), wherein an $R_4$-substituted thiolactam is allowed to react with methyl iodide, and Example XX, wherein an S-Me thiolactim ether, in free base form, is allowed to react with an $R_4$-alkylating agent, are obtained the following starting materials of formula (II).

| | Starting Material | Alkylating Agent | II |
|---|---|---|---|
| 1. | 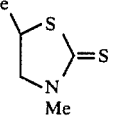 | $Me_3O^+BF_4^-$ | 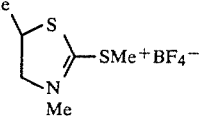 |
| 2. | 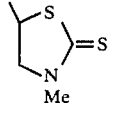 | MeI | 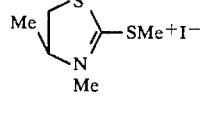 |
| 3. | 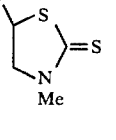 | $MeOSO_2F$ | 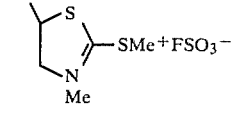 |
| 4. | 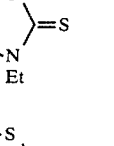 | MeI | 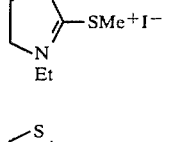 |
| 5. | 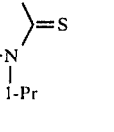 | MeI | 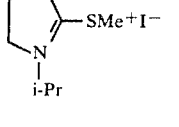 |

-continued

| | Starting Material | Alkylating Agent | II |
|---|---|---|---|
| 6. | thiazolidine-2-thione, N-n-C₃H₇(Pr) | MeI | 2-SMe⁺I⁻ thiazoline, N-n-Pr |
| 7. | 6-membered S,N ring with C=S, N-Et | MeI | 6-membered S,N ring, 2-SMe⁺I⁻, N-Et |
| 8. | 6-membered O,N ring with =N, SMe | EtI | 6-membered O,N ring, SMe⁺I⁻, N-Et |
| 9. | Me-substituted oxazoline, 2-SMe | n-PrI | Me-substituted oxazolidine, 2-SMe⁺I⁻, N-n-Pr |
| 10. | 4,4-diMe thiazoline, 2-SMe | MeI | 4,4-diMe thiazoline, 2-SMe⁺I⁻, N-Me |
| 11. | 4-Me thiazoline, 2-SMe | Et₃O⁺BF₄⁻ | 4-Me thiazoline, 2-SMe⁺BF₄⁻, N-Et |
| 12. | 6-Me-substituted dihydrothiazine, SMe | MeI | 6-Me dihydrothiazine, SMe⁺I⁻, N-Me |
| 13. | thiomorpholine-type, SMe | i-PrI | same, SMe⁺I⁻, N-i-Pr |
| 14. | 7-membered S,N ring, SMe | MeI | 7-membered S,N ring, SMe⁺I⁻, N-Me |
| 15. | 7-membered S,N ring, =SMe | MeOSO₂F | same, N-Me, =SMe⁺FSO₃⁻ |

| | Starting Material | Alkylating Agent | II |
|---|---|---|---|
| 16. | 6-membered ring: Me at C, O, C-SMe, N; methyl on carbon alpha to O | $Me_3O^+BF_4^-$ | Same ring with N-Me; C=SMe$^+$ BF$_4^-$ |
| 17. | 6-membered ring: Me, Me at C, O, C-SMe, N (gem-dimethyl) | $Et_3O^+BF_4^-$ | Same ring with N-Et; C=SMe$^+$ BF$_4^-$ |
| 18. | 6-membered ring: O, C-SMe, N-CH(Me) | MeI | N-Me; C=SMe$^+$ I$^-$ |
| 19. | Morpholine-type: O, C-SMe, N | n-PrI | N-n-Pr; C=SMe$^+$ I$^-$ |
| 20. | 7-membered ring: N, C-SMe, S | MeI | N-Me; C=SMe$^+$ I$^-$ |

EXAMPLE XXVII

A. Reaction of an appropriate N-unsubstituted lactam with an appropriate O-alkylating agent in dry CH$_2$Cl$_2$ under an inert atmosphere (N$_2$ or Ar), followed by conversion to the free base in the same solvent by treatment with cold aqueous alkali and drying over K$_2$CO$_3$ (anhydrous) affords, after solvent removal in vacuo, the following lactim ethers:

| | Starting Lactam | O—Alkylating Agent | Product Lactim Ether |
|---|---|---|---|
| 1. | 6-membered ring with S, C=O, NH | $Me_3O^+BF_4^-$ | 6-membered ring with S, C-OMe, N |
| 2. | 6-membered ring with S, C=O, NH (isomer) | $Et_3O^+BF_3^-$ | S, C-OEt, N |
| 3. | 6-membered ring with NH, S, C=O | $Et_3O^+BF_4^-$ | N, S, C-OEt |

-continued

| | Starting Lactam | O—Alkylating Agent | Product Lactim Ether |
|---|---|---|---|
| 4. | Me-substituted thiazepanone (S, C=O, NH) | MeOSO$_2$F | Me-substituted thiazepane-OMe (S, C-OMe, N) |
| 5. | thiazocanone (S, C=O, NH) | Me$_3$O$^+$BF$_4^-$ | thiazocane-OMe (S, C-OMe, N) |
| 6. | thiazepanone isomer (S, C=O, NH) | Et$_3$O$^+$BF$_4^-$ | thiazepane-OEt (S, C-OEt, N) |
| 7. | thiazepanone isomer (S, C=O, NH) | Et$_3$O$^+$BF$_4^-$ | thiazepane-OEt (S, C-OEt, N) |
| 8. | Me, Me-oxazolidinone cis and trans- | Me$_3$O$^+$BF$_3^-$ | Me, Me-oxazoline-OMe |
| 9. | Me, Me-oxazolidinone | Et$_3$O$^+$BF$_4^-$ | Me, Me-oxazoline-OEt |
| 10. | Me, Me-oxazolidinone | Et$_3$O$^+$BF$_4^-$ | Me, Me-oxazoline-OEt |
| 11. | oxazinanone | Et$_3$O$^+$BF$_4^-$ | oxazine-OEt |
| 12. | Me-oxazinanone | MeOSO$_2$F | Me-oxazine-OMe |
| 13. | Me, Me-oxazinanone | Me$_3$O$^+$BF$_4^-$ | Me, Me-oxazine-OMe |

-continued

| | Starting Lactam | O—Alkylating Agent | Product Lactim Ether |
|---|---|---|---|
| 14. | Me, H on 6-membered ring with O, N, C=O | $Et_3O^+BF_4^-$ | Me, on 6-membered ring with O, N, C-OEt |
| 15. | Me-substituted 7-membered ring with O, NH, C=O | $Et_3O^+BF_4^-$ | Me-substituted 7-membered ring with O, N, C-OEt |
| 16. | 7-membered ring with O, NH, C=O | $MeOSO_2F$ | 7-membered ring with O, N, C-OMe |
| 17. | 6-membered ring with O, NH, C=O | $Et_3O^+BF_4^-$ | 6-membered ring with O, N, C-OEt |

B. Treatment of an $R_4$-substituted lactam with an appropriate O-alkylating agent (C.f. Ex. XII), or a lactim ether with an appropriate N-alkylating agent ($R_4Y$) affords the following II starting materials, where X=OEt or OMe:

| | N—$R_4$ Lactam or Lactim Ether | Alkylating Agent | II |
|---|---|---|---|
| 1. | Thiazolidinone, N-Me | $Et_3O^+BF_4^-$ | Thiazoline, N-Me, C-OEt $^+BF_4^-$ |
| 2. | Oxazolidinone, N-Et | $Me_3O^+BF_4^-$ | Oxazoline, N-Me, C-OMe $^+BF_4^-$ |
| 3. | 6-membered ring with O, N-Me, C=O | $MeOSO_2F$ | 6-membered ring with O, N-Me, C-OMe $^+FSO_3^-$ |
| 4. | Me, Me, N on 6-membered ring with S, C=O | $Et_3O^+BF_4^-$ | Me, Me, N on 6-membered ring with S, C-OEt $^+BF_4^-$ |
| 5. | 6-membered ring with S, N, C-OEt | $MeOSO_2F$ | 6-membered ring with S, N-Me, C-OEt $^+FSO_3^-$ |

-continued

| | N—R$_4$ Lactam or Lactim Ether | Alkylating Agent | II |
|---|---|---|---|
| 6. | [structure: S-containing 6-ring with OEt, N] | Et$_3$O$^+$BF$_4^-$ | [structure with OEt$^+$BF$_4^-$, N-Et] |
| 7. | [structure: S-containing 6-ring with OMe, N] | MeI | [structure with OMe$^+$I$^-$, N-Me] |
| 8. | [structure: thiomorpholine-like with OEt] | MeOSO$_2$F | [structure with OEt$^+$FSO$_3^-$, N-Me] |
| 9. | [structure: N, S ring with OEt] | Me$_3$O$^+$BF$_4^-$ | [structure with N-Me, OEt$^+$BF$_4^-$] |
| 10. | [structure: Me-substituted S ring with OMe, N] | Et$_3$O$^+$BF$_4^-$ | [structure with Me, OMe$^+$BF$_4^-$, N-Et] |
| 11. | [structure: 7-membered S,N ring with OMe] | MeOSO$_2$F | [structure with OMe$^+$FSO$_3^-$, N-Me] |
| 12. | [structure: 7-membered S,N ring with OEt] | Et$_3$O$^+$BF$_4^-$ | [structure with OEt$^+$BF$_4^-$, N-Et] |
| 13. | [structure: 7-membered S,N ring with OEt] | MeOSO$_2$F | [structure with OEt$^+$FSO$_3^-$, N-Me] |
| 14. | [structure: Me, Me oxazoline with OMe] cis- and trans- | MeOSO$_2$F | [structure with Me, Me, OMe$^+$FSO$_3^-$, N-Me] |

-continued

| N—R₄ Lactam or Lactim Ether | Alkylating Agent | II |
|---|---|---|
| 15. [4,4-dimethyl-2-ethoxy-oxazoline] | Et₃O⁺BF₄⁻ | [N-methylated product BF₄⁻] |
| 16. [5,5-dimethyl-2-ethoxy-oxazoline] | Me₃O⁺BF₄⁻ | [N-methylated product BF₄⁻] |
| 17. [2-ethoxy-5,6-dihydro-4H-1,3-oxazine] | n-PrI | [N-n-propyl product I⁻] |
| 18. [4-methyl-2-methoxy-5,6-dihydro-oxazine] | Et₃O⁺BF₄⁻ | [N-ethyl product BF₄⁻] |
| 19. [5,5-dimethyl-2-methoxy-oxazine] | i-PrI | [N-isopropyl product I⁻] |
| 20. [2-methyl-4-ethoxy-oxazine] | MeOSO₂F | [N-methyl product FSO₃⁻] |
| 21. [5-methyl-2-ethoxy-1,3-oxazepine-like] | Me₃O⁺BF₄⁻ | [N-methyl product BF₄⁻] |
| 22. [2-methoxy-oxazepine] | Et₃O⁺BF₄⁻ | [N-ethyl product BF₄⁻] |
| 23. [4-ethoxy-oxazine] | MeOSO₂F | [N-methyl product FSO₃⁻] |

| N—R₄ Lactam or Lactim Ether | Alkylating Agent | II |
|---|---|---|
| 24. 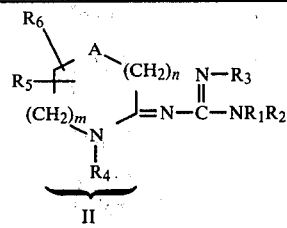 | Et₃O⁺BF₄⁻ | 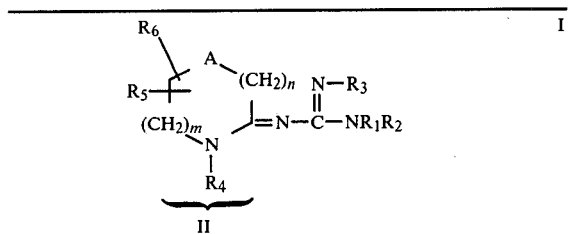 |

EXAMPLE XXVIII

Reaction of the appropriate II with the appropriate guanidine III according to the teaching of Example XXII affords the following products as the indicated acid addition salts HX:

I

| No. of II from Ex. XXVIB | NR₁R₂ | R₃ | HX |
|---|---|---|---|
| 1. | —N(morpholino, O) | 2-MePh | fumarate |
| 2. | —N(Me)(cyclopentyl) | 2-(—C(CH₃)=CH₂)Ph | HI |
| 3. | —N(thiomorpholino, S) | 3,4-(OCH₂O)Ph | HCl |
| 4. | —NEt₂ | 4-BrPh | L(+)-tartrate |
| 5. | —N(piperidino) | 4-OMePh | H₃PO₄ |
| 6. | —N(morpholino, O) | 4-MePh | H₂SO₄ |
| 7. | —N(pyrrolidino) | Ph | HI |
| 8. | —N(morpholino, O) | 4-FPh | MeSO₃H |
| 9. | —N(pyrrolidino) | 4-Cl—2-MePh | tosylate |
| 10. | —N(thiomorpholino, S) | 2,5-diMePh | 2-napsylate |
| 11. | —N(thiomorpholino, S) | 4-OEtPh | HCl |
| 12. | —NMeEt | cyclohexyl | HBr |
| 13. | —N(pyrrolidino) | —C(CH₃)₂CH₂C(CH₃)₃ | fumarate |
| 14. | —N(piperidino) | 3,4-(OCH₂O)Ph | succinate |
| 15. | —N(morpholino, O) | 3-CF₃Ph | citrate |
| 16. | —N(thiomorpholino, S) | 3-ClPh | benzoate |
| 17. | —N(Me)(cyclohexyl) | 2-Cl—5-OMePh | pamoate |

-continued

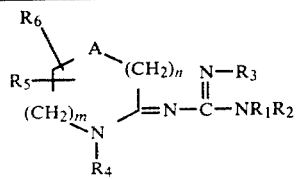

| No. of II from Ex. XXVIB | NR₁R₂ | R₃ | HX |
|---|---|---|---|
| 18. | piperidine (—N⟨⟩) | —CH(Ph)₂ | HI |
| 19. | thiomorpholine (—N⟨S⟩) | 4-MePh | $H_3PO_4$ |
| 20. | morpholine (—N⟨O⟩) | 2,5-Me₂—4-OMePh | maleate |

EXAMPLE XXIX

Utilizing the teachings of Examples IX and X and using the appropriate II, generated under these conditions, of Example XXVIIB, and the appropriate guanidine III free base, followed by conventional work-up procedures, conversion to free base, and to a pharmaceutically-acceptable salt form, gives the following products (I) in the salt form indicated:

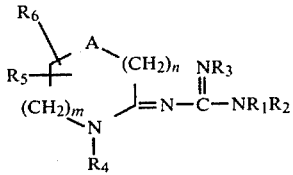

| No. of II from Ex. XXVIIB | —NR₁R₂ | R₃ | HX |
|---|---|---|---|
| 1. | morpholine | 3,4-Me₂Ph | HI |
| 2. | piperidine | 2-Cl—4-MePh | fumarate |
| 3. | thiomorpholine | 2-iPrPh | $H_2SO_4$ |
| 4. | piperidine | 3,4-(OEt)₂Ph | maleate |
| 5. | —NEt₂ | 2,5-Cl₂Ph | mesylate |
| 6. | —N(CH₃)(pyrrolidine) | 2-MePh | tosylate |
| 7. | morpholine | 3-Cl—4-FPh | benzoate |
| 8. | pyrrolidine | 4-SMePh | ethanesulfonate |
| 9. | morpholine | 2-Cl—5-OMePh | fumarate |
| 10. | morpholine | 3-MePh | HCl |
| 11. | —NMeEt | 4-ClPh | $H_2SO_4$ |
| 12. | thiomorpholine | 4-OMePh | $H_3PO_4$ |
| 13. | pyrrolidine | Ph | L(+)-tartrate |
| 14. | piperidine | 2-Me—5-ClPh | mesylate |
| 15. | thiomorpholine | 4-EtPh | maleate |
| 16. | morpholine | 2-BrPh | tosylate |

-continued

I

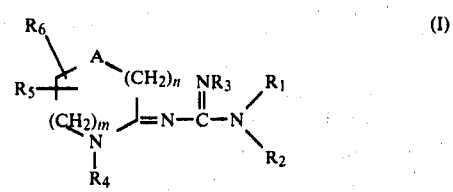

| No. of II from Ex. XXVIIB | —NR₁R₂ | R₃ | HX |
|---|---|---|---|
| 17. | —N(CH₃)— ⌬ | 4-OEtPh | succinate |
| 18. | —NEt₂ | 2-Cl—4-MePh | citrate |
| 19. | —N⟨ ⟩ (pyrrolidine) | 2,5-Me₂Ph | fumarate |
| 20. | —N⟨ ⟩S (thiomorpholine) | 4-MePh | H₂SO₄ |
| 21. | —N⟨ ⟩ (piperidine) | 2-EtPh | H₃PO₄ |
| 22. | —N⟨ ⟩S | Ph | tosylate |
| 23. | —N⟨ ⟩O | 4-MePh | L(+)-tartrate |
| 24. | —N⟨ ⟩ | 2-(—C(=CH₂)—CH₃)Ph | HCl |

EXAMPLE XXX

N-(4-Methoxyphenyl)-N'-(4,5-dimethyl-3-thiomorpholinylidene)-1-pyrrolidinecarboximidamide monohydroiodide: Triethyloxonium fluoroborate (0.0844 mol) was prepared from 15.97 g (0.1125 mol) of BF₃:Et₂O and 7.81 g (0.0844 mol) of epichlorohydrin in 150 ml of dry ether. After 2 hours, the crystals were washed 2×80 ml anh. ether, dissolved in 60 ml of dry CH₂Cl₂, and treated with a solution of a stoichiometric quantity of 4,5-dimethylthiomorpholin-3-one in 50 ml of dry CH₂Cl₂. After stirring for 2 hours at room temperature, to this reaction mixture was added a solution of 13.23 g (0.0603 mol) of N-(4-methoxy)phenyl-1-pyrrolidinecarboximidamide as the free base in 100 ml of dry CH₂Cl₂ followed by 25 g (0.18 mol) of anh. K₂CO₃. After stirring overnight, TLC indicated considerable starting material remained. The reaction mixture was filtered, and concentrated in vacuo to an oil. This was converted to free base (cold 20% NaOH, CH₂Cl₂ extraction, dried (K₂CO₃) and evaporated in vacuo, and then converted to a mixture of fumarate salts by adding 7.0 g (0.0603 mol) of fumaric acid in 100 ml hot 2-PrOH. Cooling the 2-PrOH solution gave 9.8 g (48%) of the fumarate salt of N-(4-methoxyphenyl-1-pyrrolidinecarboximidamide). The mother liquors were evaporated in vacuo, reconverted to free base as above (TLC indicated this treatment removed all but a trace of unreacted starting material). The residue was dissolved in ether and neutralized with 50% HI to give crude product as the HI salt. Recrystallization from MeOH-t-BuOH gave 8.1 g (28%) of pure title compound; m.p. 185°-187° C.

I claim:

1. A heterocyclic derivative of guanidine selected from the group consisting of a compound having the formula:

(I)

$$\begin{array}{c}R_6\\ \diagdown\\ R_5\text{---}\!\!\begin{array}{c}A\\ |\\ (CH_2)_m\end{array}\!\!\begin{array}{c}(CH_2)_n\\ \diagdown\\ \diagup\end{array}\!\!=\!\!N\!-\!\overset{NR_3}{\underset{\parallel}{C}}\!-\!N\overset{R_1}{\underset{R_2}{\diagdown}}\\ \underset{R_4}{N}\end{array}$$

and the pharmaceutically acceptable acid addition salts thereof wherein:
A is a member selected from the group consisting of O and S;
n is the integer 0, 1, 2, 3;
m is the integer 0, 1, 2, 3, provided that n+m=1, 2, or 3;
R₁ is a member selected from the group consisting of methyl and ethyl;
R₂ is a member selected from the group consisting of loweralkyl, cyclopentyl, cyclohexyl, and benzyl;

taken together represents a member selected from the group consisting of:

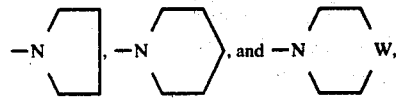

wherein W is a member selected from the group consisting of O, S, N-loweralkyl and N-aryl; and
R₃ is a member selected from the group consisting of:
alkyl having from 4 to 10 carbons;
phenyl, methylenedioxypheny; phenyl substituted with from 1 to 3 substituents each selected from the group consisting of halo, loweralkyl and loweralkoxy; phenyl substituted with a member selected from the group consisting of hydroxy, benzyloxy, loweralkanoyloxy, nitro; trifluoromethyl and methylthio;
naphthyl;
cyclopentyl; cyclohexyl;
exo-2-norbornyl; endo-2-norbornyl; 1-adamantyl;
arylalkyl in which the aryl function is phenyl and the alkyl function has from 1 to 4 carbons; and diphenylalkyl in which the alkyl function has from 1 to 2 carbons;

$R_4$ is a member selected from the group methyl, ethyl, n-propyl, i-propyl, n-butyl and isobutyl;

$R_5$ is H or loweralkyl having from 1 to 4 carbons; and $R_6$ is H or loweralkyl having from 1 to 4 carbons.

2. A compound selected from the group consisting of N-(3-methyl-2-thiazolidinylidene)-N'-phenyl-1-pyrrolidinecarboximidamide and the pharmaceutically-acceptable acid addition salts thereof.

3. A compound selected from the group consisting of N-(3-methyl-2-thiazolidinylidene)-N'-phenyl-4-morpholinecarboximidamide and the pharmaceutically-acceptable acid addition salts thereof.

4. A compound selected from the group consisting of N-(4-methoxyphenyl)-N'-(3-methyl-2-thiazolidinylidene)-1-piperidinecarboximidamide and the pharmaceutically-acceptable acid addition salts thereof.

5. A compound selected from the group consisting of N-(3-methyl-2-oxazolidinylidene)-N'-phenyl-1-pyrrolidinecarboximidamide and the pharmaceutically-acceptable acid addition salts thereof.

6. A compound selected from the group consisting of N-(2,3,5,6-tetrahydro-4-methyl-1,4-oxazine-3-ylidene)-N'-phenyl-1-pyrrolidinecarboximidamide and the pharmaceutically acceptable acid addition salts thereof.

7. A compound selected from the group consisting of N-(4-hydroxyphenyl)-N'-(3-methyl-2-thiazolidinylidene)-1-piperidinecarboximidamide and the pharmaceutically-acceptable acid addition salts thereof.

8. A compound selected from the group consisting of N-{[(2,3,5,6-tetrahydro)-4-methyl]-1,4-thiazin-3-ylidene}-N'-(4-methoxyphenyl)-1-piperidinecarboximidamide and the pharmaceutically-acceptable acid addition salts thereof.

9. A compound selected from the group consisting of N-(4-methoxyphenyl)-N'-(4,5-dimethyl-3-thiomorpholinylidene)-1-pyrrolidinecarboximidamide and the pharmaceutically-acceptable acid addition salts thereof.

10. A compound selected from the group consisting of N'-(4-methylphenyl)-N-(3-methyl-2-thiazolidinylidene-4-morpholinecarboximidamide and the pharmaceutically-acceptable acid addition salts thereof.

11. A compound selected from the group consisting of N-(3-methyl-2-thiazolidinylidene)-N'-(3,4-methylenedioxyphenyl)-4-morpholinecarboximidamide and the pharmaceutically-acceptable acid addition salts thereof.

12. A compound of formula (II) or a pharmaceutically acceptable acid addition salt thereof:

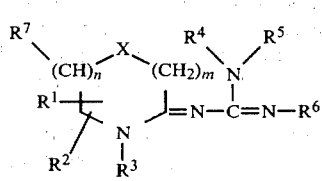

wherein

X represents oxygen or sulfur;

n represents zero, 1, 2 or 3;

m represents zero, 1, 2 or 3, provided that m+n=1, 2, or 3;

$R^7$ represents hydrogen or $C_{1-4}$ alkyl;

$R^1$ and $R^2$ are the same or different and represent hydrogen or $C_{1-4}$ alkyl, and at least one of $R^7$, $R^1$ or $R^2$ is hydrogen;

$R^3$ represents methyl, ethyl, n-propyl, iso-propyl, n-butyl and isobutyl;

$R^4$ represents $C_{1-2}$ alkyl;

$R^5$ represents $C_{1-4}$ alkyl; $C_{3-6}$ cycloalkyl; or aralkyl in which the aryl function is a member selected from phenyl and naphthyl and the alkyl group has from 1 to 4 carbon atoms; or $R^4$ and $R^5$ together represent the remaining members of a 5- or 6-membered ring, the latter ring optionally containing an oxygen, sulfur or additional nitrogen atom at the 4-position relative to the first nitrogen atom, said additional nitrogen, when present, being the nitrogen of N-$C_{1-4}$ alkyl or N-aryl in which the aryl function is a member selected from phenyl and naphthyl; and $R^6$ represents phenyl, optionally substituted with up to 3 groups selected from halogen, $C_{1-4}$ alkyl, $C_{1-4}$ alkoxy, or phenyl substituted with a member selected from hydroxy, benzyloxy, $C_{1-4}$ alkanoyloxy, nitro, trifluoromethyl, methylthio and isopropenyl; methylenedioxyphenyl; $C_{4-10}$ alkyl; naphthyl; $C_{5-8}$ cycloalkyl; exo-2-norbornyl, endo-2-norbornyl; 1-adamantyl; arylalkyl in which the aryl function is a member selected from phenyl and naphthyl and the alkyl group has from 1 to 4 carbon atoms; and diphenylalkyl in which the alkyl function has 1 to 2 carbons.

13. A compound as claimed in claim 12 wherein n is 1 and m is zero.

14. A compound as claimed in claim 12 wherein $R^7$ is hydrogen, and m+n=2.

15. A compound as claimed in claim 12 selected from the following or their pharmaceutically acceptable acid addition salts thereof:

N-(3-methylthiazolidin-2-ylidene)-N'-phenyl-1-pyrrolidine carboxamidine;

N-(3-methylthiazolidin-2-ylidene)-N'-(4-methoxyphenyl)-1-piperidine carboxamidine;

N-(3-methylthiazolidin-2-ylidene)-N'-(3-chloro-4-methylphenyl)-1-(4-methylpiperazine) carboxamidine;

N-(3-methylthiazolidin-2-ylidene)-N'-phenyl-1-morpholine carboxamidine;

N-(3-methylthiazolidin-2-ylidene)-N'-(3-ethylphenyl)-1-pyrrolidine carboxamidine;

N-(3-methylthiazolidin-2-ylidene)-N'-(2-chlorophenyl)-1-pyrrolidine carboxamidine;

N,N-diethyl-N'-(3-ethylthiazolidin-2-ylidene)-N''-(4-bromophenyl)guanidine;

N-(3-methylthiazolidin-2-ylidene)-N'-(4-trifluoromethylphenyl)-1-thiomorpholine carboxamidine;

N'-(2-chlorophenyl)-N-(3-methylthiazolidin-2-ylidene)-1-morpholine carboxamidine;

N'-(4-bromophenyl)-N-(3-methylthiazolidin-2-ylidene)-1-(4-phenylpiperazine) carboxamidine;

N'-(4-bromo-3-chlorophenyl)-N-(3-methylthiazolidin-2-ylidene)-1-pyrrolidine carboxamidine;

N,N-diethyl-N'-(3-methylthiazolidin-2-ylidene)-N''-(2-chloro-5-trifluoromethylphenyl)guanidine;

N'-(2,4-difluorophenyl)-N-(3-methylthiazolidin-2-ylidene)-1-morpholine carboxamidine; and N-(3-methyloxazolidin-2-ylidene)-N'-phenyl-1-pyrrolidine carboxamidine.

16. A compound of formula (II) or a pharmaceutically acceptable acid addition salt thereof:

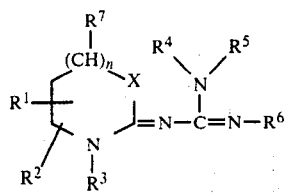

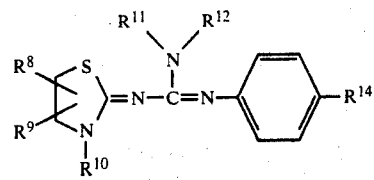

wherein
- X represents oxygen or sulfur;
- n represents zero or 1;
- $R^7$ represents hydrogen or $C_{1-4}$ alkyl;
- $R^1$ and $R^2$ are the same or different and represent hydrogen or $C_{1-4}$ alkyl, and at least one of $R^7$, $R^1$ or $R^2$ is hydrogen;
- $R^3$ represents methyl, ethyl, n-propyl, iso-propyl, n-butyl and isobutyl;
- $R^4$ represents $C_{1-2}$ alkyl;
- $R^5$ represents $C_{1-4}$ alkyl; $C_{3-6}$ cycloalkyl; or aralkyl in which the aryl function is a member selected from phenyl and naphthyl and the alkyl group has from 1 to 4 carbon atoms; or $R^4$ or $R^5$ together represent the remaining members of a 5- or 6-membered ring, the latter ring optionally containing an oxygen, sulfur or additional nitrogen atom at the 4-position relative to the first nitrogen atom, said additional nitrogen, when present, being the nitrogen of N-$C_{1-4}$ alkyl or N-aryl in which the aryl function is a member selected from phenyl and naphthyl; and
- $R^6$ represents phenyl, optionally substituted with up to 3 groups selected from halogen, $C_{1-4}$ alkyl, $C_{1-4}$ alkoxy, or phenyl substituted with a member selected from hydroxy, benzyloxy, $C_{1-4}$ alkanoyloxy, nitro, trifluoromethyl, methylthio and isopropenyl; and methylenedioxyphenyl.

17. A compound as claimed in claim 16 wherein $R^1$ and $R^2$ represent hydrogen.

18. A compound as claimed in claim 16 wherein $R^3$ represents methyl, ethyl, n-propyl, iso-propyl, n-butyl or isobutyl.

19. A compound as claimed in claim 18 wherein $R^3$ represents methyl or ethyl.

20. A compound as claimed in claim 16 wherein $R^4$ and $R^5$ together represent the remaining members of a 5- or 6-membered ring, the latter ring optionally containing an oxygen, sulfur or additional nitrogen atom at the 4-position relative to the first nitrogen atom, said additional nitrogen, when present, being the nitrogen of N-$C_{1-4}$ alkyl or N-aryl in which the aryl function is a member selected from phenyl and naphthyl.

21. A compound as claimed in claim 20 wherein $R^4$ and $R^5$ complete a pyrrolidine, piperidine, morpholine, thiomorpholine, 4($C_{1-4}$ alkyl)piperazine or 4(phenyl)-piperazine.

22. A compound as claimed in claim 20 wherein the ring is unsubstituted, or substituted on said optional, additional nitrogen atom, when present, with $C_{1-4}$ alkyl or phenyl.

23. A compound as claimed in claim 16 wherein $R^4$ and $R^5$ together represent —$(CH_2)_4$—, —$(CH_2)_2O(CH_2)_2$—, or —$(CH_2)_2 NR_x(CH_2)_2$— in which $R_x$ is $C_{1-4}$ alkyl or aryl in which the aryl function is a member selected from phenyl and naphthyl.

24. A compound as claimed in claim 16 having formula (III) or a pharmaceutically acceptable acid addition salt thereof:

wherein
- $R^8$ and $R^9$ represent hydrogen or $C_{1-4}$ alkyl;
- $R^{10}$ is selected from the group consisting of methyl, ethyl, n-propyl, iso-propyl, n-butyl and isobutyl;
- $R^{11}$ and $R^{12}$ together represent the remaining members of a 5- or 6-membered ring, the latter ring optionally containing an oxygen or an additional nitrogen atom at the 4-position relative to the first nitrogen atom, said additional nitrogen atom, when present, being the nitrogen atom of N-$C_{1-4}$ alkyl of N-aryl in which the aryl function is a member selected from phenyl and naphthyl; and
- $R^{14}$ represents hydrogen, $C_{1-4}$ alkyl, halogen, trifluoromethyl, methylthio, isopropenyl or benzyloxy.

25. A compound as claimed in claim 16 wherein n is zero.

26. A compound as claimed in claim 16 wherein $R^7$ is hydrogen and n is one.

27. A compound as claimed in claim 16 selected from the following or their pharmaceutically acceptable acid addition salts thereof:
- N-(3-methylthiazolidin-2-ylidene)-N'-phenyl-1-pyrrolidine carboxamidine;
- N-(3-methylthiazolidin-2-ylidene)-N'-phenyl-1-morpholine carboxamidine;
- N-(3-methylthiazolidin-2-ylidene)-N'-(2-chlorophenyl)-1-pyrrolidine carboxamidine; and
- N-(3-methyloxazolidin-2-ylidene)-N'-phenyl-1-pyrrolidine carboxamidine.

28. A compound of the formula

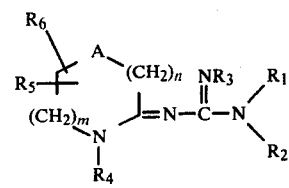

and the pharmaceutically acceptable acid addition salts thereof wherein:
- A is a member selected from the group consisting of O and S;
- n is the integer 0, 1, 2 or 3;
- m is the integer 0, 1, 2 or 3, provided that when n is 0, m=3; when n is 1, m=1 or 2; when n is 2, m=0 or 1; and when n is 3, m=0;
- $R_1$ is a member selected from the group consisting of methyl and ethyl;
- $R_2$ is a member selected from the group consisting of loweralkyl, cyclopentyl, cyclohexyl and benzyl;
- $R_1$ and $R_2$ taken together with the commonly attached nitrogen atom, represents a member selected from the group consisting of:

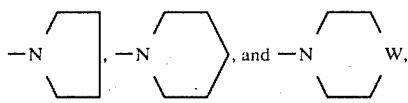

wherein W is a member selected from the group consisting of O, S, N-loweralkyl and N-aryl;

$R_3$ is a member selected from the group consisting of phenyl, methylenedioxyphenyl, phenyl substituted with from 1 to 3 substituents each selected from the group consisting of halo, loweralkyl, and loweralkoxy; and phenyl substituted with a member selected from the group consisting of hydroxy, benzyloxy, loweralkanoyloxy, nitro trifluoromethyl and methylthio;

$R_4$ is a member selected from the group consisting of methyl, ethyl, n-propyl, i-propyl, n-butyl and isobutyl;

$R_5$ is H or loweralkyl having from 1 to 4 carbons; and
$R_6$ is H or loweralkyl having from 1 to 4 carbons.

29. A pharmaceutical composition for the treatment of diabetes which comprises a compound, or a pharmaceutically acceptable acid addition salt thereof, as claimed in claim 16 together with a pharmaceutical carrier or excipient said compound or salt being present in an amount effective against diabetes.

30. An anti-diabetic composition according to claim 29 in orally or parenterally administrable form.

31. An antidiabetic composition in which the anti-diabetic agent is a compound of claim 27 and is present in an amount effective against diabetes.

32. A method of treating diabetes which comprises administering orally or parenterally to a diabetic host in need thereof an anti-diabetic amount of a composition of claim 29.

33. A method according to claim 32 wherein the composition is in unit dosage form.

* * * * *